(12) United States Patent
Bell

(10) Patent No.: US 8,129,313 B2
(45) Date of Patent: Mar. 6, 2012

(54) AQUEOUS AGROCHEMICAL CONCENTRATE COMPOSITION

(75) Inventor: Gordon Alastair Bell, Bracknell (GB)

(73) Assignee: Syngenta Crop Protection, Inc., Greensboro, NC (US)

( * ) Notice: Subject to any disclaimer, the term of this patent is extended or adjusted under 35 U.S.C. 154(b) by 1111 days.

(21) Appl. No.: 10/525,161

(22) PCT Filed: Aug. 12, 2003

(86) PCT No.: PCT/GB03/03499
§ 371 (c)(1),
(2), (4) Date: Feb. 22, 2005

(87) PCT Pub. No.: WO2004/017733
PCT Pub. Date: Mar. 4, 2004

(65) Prior Publication Data
US 2006/0003897 A1    Jan. 5, 2006

(30) Foreign Application Priority Data
Aug. 22, 2002 (GB) .................................. 0219610.3

(51) Int. Cl.
*A01N 25/04* (2006.01)
*A01N 25/16* (2006.01)
*A01N 25/28* (2006.01)
(52) U.S. Cl. ........................................ 504/364; 504/359
(58) Field of Classification Search .................. 504/364, 504/359
See application file for complete search history.

(56) References Cited

U.S. PATENT DOCUMENTS

| | | | |
|---|---|---|---|
| 4,517,201 A * | 5/1985 | Kerry et al. | 514/521 |
| 4,808,408 A * | 2/1989 | Baker et al. | 424/408 |
| 4,853,228 A * | 8/1989 | Wallach et al. | 424/450 |
| 4,936,901 A | 6/1990 | Surgant, Sr. et al. | |
| 5,229,122 A * | 7/1993 | Chadwick et al. | 424/408 |
| 5,393,791 A * | 2/1995 | Roberts | 514/762 |
| 6,730,635 B2 * | 5/2004 | Wolf et al. | 504/359 |
| 2005/0221991 A1 * | 10/2005 | Wolf et al. | 504/359 |

FOREIGN PATENT DOCUMENTS

| | | |
|---|---|---|
| GB | 1513614 | 6/1978 |
| JP | 6256116 | 9/1994 |
| WO | 9513698 | 5/1995 |
| WO | 03/099005 A1 | 5/2003 |

OTHER PUBLICATIONS chemical adjuvant, http://medical-dictionary.thefreedictionary.com/chemical+adjuvant, 4 pages.*
Pesticide Adjuvants, The Pesticide Review, vol. 2 Issue 8, pp. 1-3, 2003.*
Nelson, Chemical Nature of Surfaces and Surfactants, Tables of Properties, Dispersing Powders in Liquids, Part 3, http://www.erpt.org/032Q/nelsc-00.htm, 2003.*
Database CA 'Online! Chemical Abstracts Service, Columbus, Ohio, US; Ootsubo, Toshiro et al: "Microcapsules containing carbamate insecticides and nonarom. esters"; retrieved from STN Database accession No. 121:295141.
*Bayer Cropscience AG v. Syngenta Limited*; Opposition Proceedings/decision in the EP, 2010.
Rompp-Lexikon Chemie, 10th edition 1998, vol. 5, P1-5, heading: "Suspension", pp. 4337-4338.
Safety data sheet pursuant to EC Directive 91/155/EEC regarding rapeseed oil.
Rompp-Lexikon Chemie, 10th edition 1997, vol. 2 Cm-G, heading: "Emulsion", pp. 1151-1152.
Printout from Wikipedia, heading: "HLB-Wert".
S. Sajjadi, et al., "Phase inversion in p-xylene/water emulsions with the non-ionic surfactant pair sorbitain monolaurate/ polyoxyethylene sorbitan monolaurate" (Span 20/Tween 20), Colloids and Surfaces A: Physiochem. Eng. Aspects 218, 2003, pp. 241-254.
Data sheet regarding Orefa® Tebuconozol.
Mollet, H.; Grubenmann, A.: "Formulierungstechnik, Emulsionen, Suspensionen, Feste Formen", Wiley-VCH Weinheim, 1st edition 1999, pp. 68-73.
Data sheet regarding Ethomeen® S/12.
Kosswig, K.; Stache, H.: "die Tenside", Carl Hanser Verlag, Munich, Vienna, 1993, pp. 228-233.
Dorfler, H. D.: "Grenzflachen und kolloid disperse Systeme", Springer Verlag, Berlin Heidelberg, 2002, pp. 336-341, chapter 9.3.
Database CA 'Online! Chemical Abstracts Service, Columbus, Ohio, US; Ootsubo, Toshiro et al: "Microcapsules containing carbamate insecticides and nonarom. esters"; retrieved from STN Database accession No. 121:295141.

* cited by examiner

*Primary Examiner* — Johann Richter
*Assistant Examiner* — Thor Nielsen
(74) *Attorney, Agent, or Firm* — William A. Teoli, Jr.

(57) ABSTRACT

An aqueous agrochemical composition and in particular an agrochemical concentrate comprises (a) a non-encapsulated aqueous solution or dispersion of an agrochemical and (b) a suspension in said aqueous solution or dispersion of a microencapsulated liquid, water-insoluble, bioperformance-enhancing adjuvant for said agrochemical. The adjuvant suitably has little or no surfactant properties. The invention permits oil adjuvants such as "Turbocharge" and "Brij 92" to be built into agrochemical compositions with which they would normally be incompatible. With certain adjuvants reduced phytotoxicity may be observed.

10 Claims, No Drawings

AQUEOUS AGROCHEMICAL CONCENTRATE COMPOSITION

This application is a 371 of International Application No. PCT/GB03/003499 filed Aug. 12, 2003, which claims priority to GB 0219610.3, filed Aug. 22, 2002, the contents of which are incorporated herein by reference.

This invention relates to a composition and in particular to a microencapsulated adjuvant composition.

It is well known that active ingredients such as agrochemicals, pharmaceuticals, inks, and dyes may be formulated such that the active composition is contained within a microcapsule shell wall. Frequently the microcapsule shell wall is designed to provide controlled release as the active composition diffuses slowly through the wall or the wall is slowly degraded. There are also applications however such as those described in WO 97/44125 in which the microcapsule provides temporary protection only and is degraded relatively rapidly as soon as the composition is put into use.

Microencapsulated compositions frequently incorporate non-biologically active surface-active polymers to assist in the suspension of the microcapsules, for example in an aqueous dispersion. Numerous surfactants and adjuvants are known which enhance the bioperformance of pharmaceuticals and agrochemicals. Care must be taken however in the use of bioperformance enhancing surfactants in microencapsulated compositions since such surfactants often locate themselves at the oil/water interface during the encapsulation process and tend to interfere with the wall-forming reaction.

According to the present invention there is provided an agrochemical composition comprising (a) a non-encapsulated aqueous solution or dispersion of an agrochemical and (b) a suspension in said aqueous solution or dispersion of a microencapsulated liquid, water-insoluble, bioperformance-enhancing adjuvant for said agrochemical.

As used herein the term aqueous "dispersion" of an agrochemical includes any form of aqueous dispersion such as dispersion of a solid in the aqueous phase or dispersion of a liquid agrochemical in water in the form of an emulsion.

The adjuvant should not interfere significantly with the microencapsulation wall-forming process. As examples of suitable adjuvants that will not interfere significantly with the wall-forming process are adjuvants have little, if any surfactant properties. Typically, the adjuvant will have a Hydrophile/Lipophile balance of 9 or less. Some of the materials that come into this category will reduce interfacial tension however they would not be effective as dispersants for oil in water emulsions. It is to be understood that the term "water-insoluble" liquid adjuvant as used herein should not be taken as indicating that the solubility of the adjuvant in water is immeasurably small but rather that there is no significant loss of the adjuvant into an aqueous phase. Typically the solubility of the adjuvant in water will be less than 0.1% by weight and preferably less than 0.01% by weight. Mixtures of liquid water-insoluble adjuvants may also be used.

Water-insoluble liquid adjuvants (oils) are normally difficult to incorporate in aqueous agrochemical formulations, particularly if the composition is a concentrate that is designed to be diluted prior to use. Such oils may also be incompatible for example with agrochemicals that are high electrolytes such as glyphosate or paraquat. Water-insoluble liquid adjuvants, even when they can be utilised, therefore tend to be added as a tank mix by the farmer rather than in the more convenient form of a "built-in" concentrate. Furthermore even adjuvant compositions designed to be added as a tank mix tend to be a complex mixture having components such as surfactants whose purpose is to increase the compatibility of the primary liquid adjuvant.

Thus whilst there are advantages in forming a composition of the invention as a tank mix for direct application, the benefits of the invention are most apparent when utilised in the form of an agrochemical concentrate designed for dilution prior to application.

Thus according to a further aspect of the present invention there is provided an aqueous agrochemical concentrate comprising (a) a non-encapsulated aqueous solution or dispersion of an agrochemical and (b) a suspension in said aqueous solution or dispersion of a microencapsulated liquid, water-insoluble, bioperformance-enhancing adjuvant for said agrochemical.

By the term "agrochemical concentrate" is meant a concentrated composition designed to be diluted with water prior to application. The actual concentration of the agrochemical in the concentrate will depend on the nature of the agrochemical and the desired concentration of the agrochemical as diluted in the spray tank. Typically the concentration of the agrochemical in the concentrate ranges from 1 to 500 g/l for example from 10 to 500 g/l and more particularly from 10 to 300 g/l. We have found that liquid water-insoluble adjuvants may be "built-in" to such concentrates according to the present invention at far higher adjuvant concentration than would be possible using conventional techniques (or in the alternative the adjuvant may be used in the presence of higher concentrations of agrochemical than would be possible using conventional techniques).

Although the adjuvant will generally act with the agrochemical to enhance its bioperformance, we have found that surprisingly the greatly increased stability of concentrates of the present invention containing high levels of adjuvant/agrochemical comes without any significant loss in activity as compared with corresponding levels of non-encapsulated adjuvant added as a tank mix. Indeed in general we have observed that the activity of agrochemicals is fully equivalent to that of corresponding levels of non-encapsulated adjuvant added as a tank mix and on some species may even be higher. Whilst there may be situations in which it is desirable to achieve controlled release of the adjuvant as compared with the agrochemical, it is generally preferred to utilise a microcapsule wall which is sufficiently robust to remain intact in the concentrate but which does not significantly retard the release rate of the adjuvant once the composition is applied to the plant. Techniques for achieving such relatively rapid release are known in the art and are described for example in EP 0902724.

Compositions of the present invention (whether concentrates or otherwise) may show a range of other beneficial effects. Whilst the scope of the present invention is not to be taken to be limited by any one particular theory, it is possible that advantages arise from the slight delay between the contact of the agrochemical with the plant surface and the release of the adjuvant. Alternatively advantages may arise from the absence of surfactants whose purpose is as compatibility aids rather than to provide bioperformance enhancement. We have observed for example that slight phytoxicity, which may occur when conventional fungicide compositions are applied to a plant, may be significantly reduced using compositions of the present invention.

Suitable water-insoluble adjuvants having little or no surfactant properties will be known to those skilled in the art. One particularly suitable class has the formula

R—X (I)

and alkoxylated derivatives thereof wherein R is a branched or straight chain alkyl or akenyl group having from 12 to 20 carbon atoms and X is hydroxy, amine (primary, secondary, tertiary or quaternary), amine oxide, phosphonate, phosphate, phosphate ester, thiol, sulphoxide, sulphone, sulphonate, sulphate, heterocyclic moiety (imidazoline, morpholine, pyrrolidone, piperazine etc), glucoside, polyglucoside or alkylated gucoside, sarcosinate, betaine (including sulpho and phospho betaines), amidoamines, carboxylic acid, amide, ester and combinations of these groups such as ether sulphates, amines, carboxylates and phosphonates. The group —X may be alkoxylated provided this does not raise the HLB much above 9. The alkoxy group will generally contain from 2 to 4 carbon atoms. In particular samples with an average of 1 to 2 ethoxy groups may generally be incorporated without imparting significant surfactant properties. Propoxy groups or butyloxy groups generally do not have the effect of imparting surfactant properties and it is possible therefore to introduce a greater number of such groups provided that the adjuvant remains a liquid. Typically there may be introduced form 1 to 20 such groups.

R is preferably a branched or straight chain alkyl or alkenyl group containing from 16 to 20 carbon atoms. When R is an alkenyl group it may have one or more double bonds which may be in either cis or trans configuration(s). Preferably R has from 1 to 3 double bonds. It is generally preferred that the double bond(s) are in the cis configuration. It is especially preferred that R is a $C_{18}$ branched chain alkyl or $C_{18}$ alkenyl group for example oleyl or isostearyl. In all the above, R may be optionally alkoxylated.

Especially preferred adjuvants are oleyl alcohol or stearyl alcohol, optionally alkoxlated with from 0 to 2 ethoxy groups; and oleic acid or stearic acid and C1 to C4 alkyl esters thereof.

As examples of adjuvants suitable for use in the composition of the present invention there may be mentioned:

"Brij" 92, oleyl alcohol ethoxylate with an average of 2 moles of ethoxylate
"Adol" 320, oleyl alcohol
"Priolene" 6910, oleic acid
"Turbocharge", proprietary blend of oils and short chain ethoxylates
"Merge", proprietary blend of oils and short chain ethoxylates
"Dash", proprietary blend of oils and short chain ethoxylates
"Silwet" L77, ethoxylated silicone
"Ethomeen" S12, Short chain ethoxylated fatty amine
"Hystrene" 9018, Stearic acid.

Also suitable are novel adjuvants disclosed in our co-pending application GB 0121580.5. Thus suitable adjuvants may have the formula

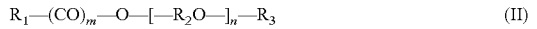

$$R_1-(CO)_m-O-[-R_2O-]_n-R_3 \quad (II)$$

wherein $R_1$ is a $C_{16}$ to $C_{20}$ straight or branched chain alkyl or alkenyl group, $R_2$ is ethyl or isopropyl, n is from 8 to 30 and m is 0 or 1 and when $R_2$ is ethyl, $R_3$ is a $C_1$ to $C_7$ alkyl group and when $R_2$ is isopropyl, $R_3$ is hydrogen or a $C_1$ to $C_7$ alkyl group.

Those skilled in the art will be able to select the adjuvant class that is most suitable for a given active ingredient. For example adjuvants particularly suitable for enhancing the bioperformance of lipophilic agrochemicals include the commercial blends "Turbocharge", "Dash", LI 700 and "Merge" and single component adjuvants such as methyl oleate, oleyl alcohol and "Brij" 92.

Examples of suitable agrochemicals include:
(a) herbicides such as fluzifop, mesotrione, fomesafen, tralkoxydim, napropamide, amitraz, propanil, cyprodanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyclodim, sethoxydim, tepraloxydim, pendimethalin, dinoterb, bifenox, oxyfluorfen, acifluorfen, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron, metoxuron, N-phosphonomethylglycine and its salts (glyphosate), glufosinate, chlormequat chloride, paraquat, diquat, trifloxysulfuron, fomesafen, mesotrione and fenuron;

(b) fungicides such as azoxystrobin, trifloxystrobin, kresoxim methyl, famoxadone, metominostrobin and picoxystrobin, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin, prothioconazole, 8-(2,6-diethyl-4-methyl-phenyl)tetrahydropyrazolo[1,2-d][1,4,5]oxadiazepine-7, 9-dione, 2,2,-dimethyl-propionic acid-8-(2,6-diethyl-4-methyl-phenyl)-9-oxo-1,2,4,5-tetrahydro-9H-pyrazolo[1,2-d][1,4,5]oxadiazepine-7-yl ester and metalaxyl; and (c) insecticides such as abamectin, acephate, acetamiprid, acrinathrin, alanycarb, aldicarb, allethrin, alpha-cypermethrin, amitraz, asulam, azadirachtin, azamethiphos, azinphos-ethyl, azinphos-methyl, bendiocarb, benfuracarb, bensultap, beta-cyfluthrin, beta-cypermethrin, bifenthrin, bioallethrin, bioresmethrin, bistrifluron, borax, buprofezin, butoxycarboxim, cadusafos, carbaryl, carbofuran, chlorpropham, clothianidin, cyfluthrin, cyhalothrin, cyprmethrin, deltamethrin, diethofencarb, diflubenzuron, dinotefuran, emamectin, endosulfan, fenoxycarb, fenthion, fenvalerate, fipronil, halfenprox, heptachlor, hydramethylnon, imidacloprid, imiprothrin, isoprocarb, lambda cyhalothrin, methamidophos, methiocarb, methomyl, nitenpyram, omethoate, permethrin, pirimicarb, pirimiphos methyl, propoxur, tebufenozide, thiamethoxam, thiodicarb, triflumoron, and xylylcarb.

The active ingredient may be in the form of an aqueous solution, a dispersion of a solid in water or an emulsion. Preferably however the active ingredient is present in the composition of the present invention as an aqueous solution of a water-soluble active or as a dispersion of a solid, insoluble active in water.

The proportion of adjuvant relative to active ingredient can readily be selected by one skilled in the art as most suitable for the active ingredient concerned to meet the intended utility. It is an advantage of the compositions of the present invention however that the concentration of the adjuvant is not limited by compatibility or stability problems when the microencapsulated adjuvant is "built-in" to the formulation. The proportion of adjuvant to active ingredient can thus mirror that found to be most useful in tank-mix application even if this content of adjuvant would be unstable when "built-in" using conventional techniques. Typically the ratio of adjuvant to active ingredient will range from 1:50 and 200:1 and preferably from 1:5 to 20:1

The adjuvants may be microencapsulated using techniques well known in the art. The process described in EP 0902724 is particularly suitable for providing rapid release of the adjuvant component but other techniques including for example coascervation may also be suitable. It will generally be convenient to prepare an aqueous microencapsulated suspension of the liquid adjuvant separately. The composition of the present invention is then conveniently formed simply by combining the aqueous microencapsulated suspension of the liquid adjuvant and the aqueous solution or suspension of the active ingredient. The ratio of the adjuvant to active ingredient and the water content of the final composition may be adjusted accordingly. Suspending or dispersion aids may be used to suspend the microcapsules and/or a water-insoluble active ingredient. It has been found that the type of dispersant used in the final mixture is not critical in determining the storage stability and quality of the formulation. Thus it is perfectly possible to include dispersants as suspending or dispersion aids at this stage that would interfere with the encapsulation process. The adjuvant will typically be emulsified using a highly water-soluble polymer such as polyvinyl alcohol. Conventional additives for agrochemical formulations may also be included in the composition.

If it is desired to obtain fast release of the adjuvant material during drying of the formulation on a leaf, or similar, surface it is necessary to have thin walled microcapsules. Typically microcapsules with a mean diameter of about 2 microns require a polymer wall concentration in the formulation of about 3% by weight. Greater quantities of polymer will slow the release rate. The diameter of the capsules and the quantity of wall forming polymer can be used to tune the performance of the capsules, depending on the required pesticide and the conditions of use.

If desired, it is possible to modify the properties of the adjuvant material by the addition of a solvent prior to encapsulation. Simple fatty alcohols such as oleyl alcohol can be encapsulated without the use of a solvent however it may be appropriate to use a water-immiscible solvent with adjuvants with ethoxylate chains. Thus a non-polar solvent such as Solvesso 200 can be used with "Brij" 92 containing microcapsules that have relatively few ethoxylate groups, whereas a more polar solvent such as a ketone is appropriate in the case of a longer chain ethoxylate such as "Silwet" L77.

The invention is illustrated by the following Examples in which all parts and percentages are by weight unless otherwise stated.

EXAMPLE 1

"Brij" 92 was weighed into a beaker (2.64 g) along with the solvent methyl cyclohexanone (1.44 g). Diphenylmethane-4, 4'-diisocyanate (MDI, "Suprasec" 2211, Huntsman Corporation) was added (0.27 g) to create a solution that was used as the oil phase in the subsequent microencapsulation process. The oil phase was added slowly and with vigorous stirring using a high shear mixer to 4.07 g of 20% w/w aqueous polyvinyl alcohol solution ("Gohsenol" GLO3, Nippon Synthetic Chemical Industry Company). When the oil phase was added the emulsion was sheared vigorously for two minutes then 0.7 g of a 10% diethylene triamine (DETA) solution was added rapidly. The resulting microcapsule suspension was diluted with 1 g of water and had the following percentage concentrations.

| Ingredient | % w/w |
|---|---|
| Brij 92 | 26 |
| Methyl cyclohexanone | 14 |
| Suprasec 2211 | 3 |
| PVA | 8 |
| DETA | 1 |
| Water | 48 |

EXAMPLES 2-7

Compositions containing microencapsulated adjuvant and suitable for use in the present invention were prepared using the general method of Example 1. The adjuvant and solvent are shown in Table 4 and proportions of wall-forming materials and other ingredients are shown in Table 5.

TABLE 4

| Example No | Pesticide | Adjuvant | Solvent |
|---|---|---|---|
| 2 | None | "Turbocharge" | Methylcyclohexanone |
| 3 | None | "Brij" 92 | Methylcyclohexanone |
| 4 | None | Oleyl alcohol | Methylcyclohexanone |
| 5 | None | "Ethomeen" S12 | Methyl cyclohexanone |
| 6 | None | Stearyl alcohol | Methyl cyclohexanone |

TABLE 5

| Example No | Adjuvant | Solvent | MDI | GLO3 | DETA | Water |
|---|---|---|---|---|---|---|
| 2 | 29.4% | 10.5% | 1.4% | 6.8% | 0.4% | 51.5% |
| 3 | 23.6% | 16.4% | 1.2% | 6.8% | 0.4% | 51.7% |
| 4 | 23.2% | 16.8% | 1.2% | 6.7% | 0.4% | 51.7% |
| 5 | 26.0% | 14.4% | 2.7% | 8.0% | 0.7% | 48.2% |
| 6 | 10.0% | 29.8% | 2.7% | 8.1% | 0.7% | 48.9% |

EXAMPLES 7-12

These Examples illustrates the incorporation of microencapsulated adjuvants into agrochemical compositions and that compositions of the present invention have a biological performance at least equivalent to the corresponding non-encapsulated composition.

EXAMPLE 7

Microencapsulated adjuvants of Examples 2, 3, and 4 were mixed into a commercial 400 g/l tralkoxydim suspension concentrate. The samples described in Examples 2, 3 and 4 which contained "Turbocharge", "Brij" 92 and oleyl alcohol respectively, were each tested as a 0.2% v/v tank mixed adjuvant. Five different rates of trakoxydim, varying from 7.5 to 50 g/ha, were sprayed in a glasshouse using a spray volume of 100 l/ha. Four weed species and a cultivar of barley that represents a volunteer cereal were tested at the 2.2 leaf growth stage. The efficacy of the herbicidal treatment was assessed after 23 days using a visual method that determined the % kill. Each experiment was replicated three times and the position of each weed sample was randomised in the glasshouse. The results are shown in the following table where the number quoted is the mean of all five tralkoxydim rates. The performance of the microencapsulated adjuvants was equivalent to that of the un-encapsulated tank mix adjuvant.

|  | AVEFA | ECHCG | LOLRI | SETVI | HORVS 'Bonanza' |
|---|---|---|---|---|---|
| Turbocharge not encapsulated | 67 | 92 | 29 | 92 | 39 |
| Oleyl alcohol microcapsules | 72 | 93 | 34 | 83 | 33 |
| Brij 92 microcapsules | 75 | 92 | 53 | 96 | 31 |
| Turbocharge microcapsules | 74 | 80 | 30 | 81 | 41 |

AVEFA *Avena fatua*
ECHCG *Echinochloa crus-galli*
LOLRI *Lolium rigidum*
SETVI *Setaria viridis*
HORVS *Hordeum vulgare*

EXAMPLE 8

A further test of the microcapsules described in Example 3 was carried out with a 400 g/l tralkoxydim suspension concentrate. Turbocharge was used as both a 0.2% and a 0.5% v/v tank mixed adjuvant standard. Five different rates of tralkoxydim, varying from 7.5 to 50 g/ha, were sprayed in a glasshouse using a spray volume of 100 l/ha. Five weed species were tested at the growth stages shown. The efficacy of the herbicidal treatment was assessed after 21 days using a visual method that determined the % kill. Each experiment was replicated three times and the position of each weed sample was randomised in the glasshouse. The results are shown in the following table where the number quoted is the mean of all five tralkoxydim levels. The performance of the microencapsulated adjuvants was equivalent to that of the un-encapsulated tank mix adjuvants.

|  | ALOMY | AVEFA | ECHCG | LOLRI | SETVI |
|---|---|---|---|---|---|
| Turbocharge not encapsulated 0.2% | 37 | 27 | 59 | 65 | 68 |
| Turbocharge not encapsulated 0.5% | 53 | 58 | 79 | 76 | 76 |
| BRIJ 92 microcapsules 0.2 % | 47 | 40 | 83 | 78 | 79 |
| BRIJ 92 microcapsules 0.5 % | 66 | 78 | 89 | 88 | 80 |

ALOMY *Alopecurus myosuroides*

EXAMPLE 9

The microencapsulated adjuvants of Example 5 were mixed into a 200 g/l potassium glyphosate formulation. The microencapsulated adjuvants of Example 5 (containing "Ethomeen" S12), was tested as a 0.2% v/v tank mixed adjuvant. Glyphosate was sprayed in a glasshouse at 200 g/ha using a spray volume of 100 l/ha. Four weed species were tested at the 2.2 leaf growth stage. The efficacy of the herbicidal treatment was assessed after 18 days using a visual method that determined the % kill. Each experiment was replicated four times and the position of each weed sample was randomised in the glasshouse. The results are shown in the following table where the number quoted is the mean of the four repeat experiments. It was not possible to incorporate "Ethomeen" S12 in the composition in non-encapsulated form, even as a tank mix. In this experiment therefore the alkyl polyglucoside "Agrimul" PG2067 was selected as a representative non-encapsulated glyphosate adjuvant. The performance of the microencapsulated adjuvant was equivalent to that of the un-encapsulated tank mix adjuvant.

| Formulation | SIDSP | ABUTH | SOLNI | IPOHE |
|---|---|---|---|---|
| "Agrimul" PG2067 not encapsulated | 59.8 | 40.0 | 70.5 | 60.0 |
| "Ethomeen" S12 microcapsules | 76.8 | 51.8 | 71.8 | 63.0 |

SIDSP *Sida spinosa*
ABUTH *Abutilon theophrasti*
SOLNI *Solanum nigrum*
IPOHE *Ipomoea hederacea*

EXAMPLE 10

The microencapsulated adjuvants of Examples 3 and 4 were tested post emergence with a commercial 240 g/l fomesafen formulation (tradename Reflex). The samples described in Examples 3 and 4 that contained "Brij" 92 and oleyl alcohol respectively, were each tested as a 0.5% v/v tank mixed adjuvant. Fomesafen was sprayed at six rates split across four species depending on susceptibility, and varying from 15 to 480 g/ha, in a glasshouse using a spray volume of 200 l/ha. Four weed species were tested at the leaf growth stages shown in the following table. The efficacy of the herbicidal treatment was assessed after 18 days using a visual method that determined the % kill. Each experiment was replicated three times. The results are shown in the following table where the number quoted is the mean of four rates and three replicates. The table indicates that the performance of the microencapsulated adjuvants was equivalent to that of the non-encapsulated tank mix adjuvant "Turbocharge" which is an industry standard.

|  | ABUTH | XANST | AMACH | CHEAL |
|---|---|---|---|---|
| Leaf growth stage | 2.35 | 2.25 | 2.6 | 2.9+ |
| No adjuvant | 36.3 | 31.7 | 66.3 | 22.9 |
| "Turbocharge" not encapsulated | 60.1 | 51 | 92.1 | 34 |
| "Brij" 92 microcapsules | 55.8 | 52.9 | 90.8 | 35.9 |
| Oleyl alcohol microcapsules | 55.8 | 46.3 | 92.2 | 37.9 |

XANST *Xanthium strumarium*
AMAGH *Amaranthus chlorostachys*
CUBAL *Chenopodeum album*

EXAMPLE 11

This Example illustrates that compositions of the present invention may show a reduced phytotoxicity when compositions containing herbicides or fungicides and certain adjuvants are applied to plants.

Azoxystrobin 250 g/l SC ("Amistar") was tested with a tank mix oil based on "Brij" 92 and compared to a formulation containing azoxystrobin SC with a microencapsulated version of the tank mix oil according to the invention. The phytotoxic response of each formulation was measured 7 days after application to barley using a percentage scoring system that reflected both coverage and severity. For each formulation the quoted results is the sum of the mean phytotocity scores for the symptoms necrosis, bleach, pinch, chlorosis and scald. The formulations were sprayed using a tracksprayer at 200 l/ha and two rates of azoxystrobin. The first rate (500 g/ha) represented double the normal rate of azoxystrobin in order to demonstrate a measurable phytotoxic response. The second rate (1000 g/ha) represented a four times excess above normal application dosage. The following table shows that the degree of phytotoxic damage produced from the microencapsulated tank mix oil was significantly less than that from the non-encapsulated sample. For comparison the results for a water spray and for Amistar suspension concentrate with a tank mix addition of a conventional non-encapsulated adjuvant, methylated rapeseed oil (0.5 v/v) are shown.

| Adjuvant | Azoxystrobin rate g ai/ha | Total Phytotoxic damage |
|---|---|---|
| Water | 0 | 1 |
| Suspension concentrate (SC) | 500 | 0 |
| | 1000 | 0 |
| SC with oil in capsules | 500 | 5 |
| | 1000 | 22 |
| SC with oil as tank mix | 500 | 69 |
| | 1000 | 130 |
| SC in methylated rapeseed oil | 500 | 48 |
| | 1000 | 79 |

These formulations were also tested under field conditions to assess the efficacy of the fungicide for the prevention of crop damage from an infestation of yellow rust, *Puccinia Striformis* (PUCCST). In each case the percentage infection has been assessed and averaged from four separate field plots. The efficacy of the microencapsulated formulation was at least as good as the non-encapsulated formulations and in each case the degree of protection was significantly better than the untreated plots. Azoxystrobin was applied at a rate of 100 g/ha.

| Pathogen | PUCCST | PUCCST |
|---|---|---|
| Assessment Location | Leaf 3 | Leaf 2 |
| Assessment Type | % disease cover (mean of results from 4 plots) | % disease cover (mean of results from 4 plots) |
| Time of assessment (days after chemical application) | 31 | 43 |
| Control treatment | 11.0 | 48.7 |
| SC with oil in capsules | 1.1 | 2.9 |
| SC with oil (not encapsulated) | 0.5 | 3.6 |
| SC in methylated rapeseed oil | 1.4 | 5.5 |

The formulations were also tested under field conditions to assess the efficacy of the fungicide for the prevention of crop damage from an infestation of *Septoria tritici* (SEPTTR). In each case the percentage infection has been assessed and averaged from four separate field plots. The efficacy of the microencapsulated formulation was at least as good as the non-encapsulated formulations and in each case the degree of protection was significantly better than the untreated plots. Azoxystrobin was applied at a rate of 150 g/ha.

| Pathogen | SEPTTR | SEPTTR |
|---|---|---|
| Assessment Location | Leaf 3 | Leaf 2 |
| Assessment Type | % disease cover (mean) | % disease cover (mean) |
| Time of assessment (days after chemical application) | 26 | 40 |
| Control treatment | 16.6 | 12.3 |
| SC with oil in capsules | 6.9 | 3.5 |
| SC with oil (not encapsulated) | 4.4 | 3.4 |
| SC in methylated rapeseed oil | 9.5 | 5.2 |

These formulations were tested under field conditions to assess the efficacy of the fungicide for the prevention of crop damage from an infestation of brown rust, PUCCRT (*Puccinia recondita*). In each case the percentage infection was assessed and averaged from four separate field plots. The efficacy of the microencapsulated formulation was at least as good as the non-encapsulated formulations and in each case the degree of protection was significantly better than the untreated plots. Azoxystrobin was applied at a rate of 100 g/ha.

| Pathogen | PUCCRT | PUCCRT |
|---|---|---|
| Assessment Location | Leaf 3 | Leaf 2 |
| Assessment Type | % disease cover (mean) | % disease cover (mean) |
| Time of assessment (days after chemical application) | 21 | 42 |
| Control treatment | 16.2 | 77.1 |
| SC with oil in capsules | 12.8 | 11.1 |
| SC with oil (not encapsulated) | 8.2 | 10.1 |
| SC in methylated rapeseed oil | 10.3 | 11.8 |

EXAMPLE 12

An adjuvant oil containing predominantly "Brij" 92 was microencapsulated according to the method shown in Example 1. The microcapsule formulation contained a concentration of 28% w/w of oil adjuvant. The formulation (945.2 g) was modified by the addition of an antisettling agent that was added as a 2% w/w solution (50.7 g) along with some water (456.7 g). The treated capsules were stirred and left for 30 minutes to equilibrate and were then added to a commercial sample of Quadris 250 g/l azoxystrobin suspension concentrate (480 g).

The final formulation contained 13.5% w/w of oil adjuvant in the form of microcapsules and 5% w/w of azoxystrobin particles. Product quality was assessed by means of visual inspection, optical microscopy after dilution, and particle size analysis. After standing undisturbed for a period of 18 months the formulation showed no signs of either separation or particle settling. The dilution properties were good and there was no evidence of crystal growth or damage to the capsule walls. An equivalent formulation, which contained the adjuvant oil as a non-encapsulated ingredient, showed signs of both settling and phase separation over the same time period.

Comparisons 1-4

These comparisons illustrates that compositions of the present invention provide stable concentrates in which the adjuvant is capable of being used and in particular "built-in" to the composition at concentrations that would not be stable using conventional techniques.

Comparison 1

As a comparison to Example 5 a sample was prepared which contained "Ethomeen" S12 in water at the same concentration as the microencapsulated sample (26% w/w). This sample gelled and was unusable, even where the solvent and/or a typical emulsifier such as "Synperonic" NP8 was added at various concentrations up to 10% w/w in an attempt to improve aqueous compatibility. "Ethomeen" S12 could not therefore be used as an agrochemical adjuvant at these concentrations in non-encapsulated form.

Comparison 2

As a comparison to Example 3 a sample was prepared which contained "Brij" 92 in water at the same concentration as the microencapsulated sample (24% w/w). This sample flocculated and was formed two separate layers. It was unusable even where the solvent and/or a typical emulsifier were added in an attempt to improve aqueous compatibility. "Brij" 92 could not therefore be used as an agrochemical adjuvant at these concentrations in non-encapsulated form. Even when using lower concentrations of non-encapsulated "Brij 92 (10% w/w and 3% w/w) it was not possible to obtain a stable composition in water. Attempts to "build-in" the adjuvant at a concentration of 10% w/w to a composition containing 5% w/w azoxystrobin similarly failed as did attempts to "build-in" the adjuvant at a concentration of 3% w/w to a composition containing 3% fomesafen.

Comparison 3

As a comparison to Example 2 a sample was prepared which contained the commercial tank mix adjuvant "Turbocharge" in water at the same concentration as the microencapsulated sample (29% w/w). This sample formed two layers and was badly flocculated which led to unacceptable thickening of the formulation. The addition of solvent and/or a typical emulsifier did not improve the flocculation problem. It was similarly not possible to obtain an stable composition of "Turbocharge" in water even at a reduced concentration of 10% w/w. Attempts to "build-in" the adjuvant at a concentration of 10% w/w to a composition containing 5% w/w azoxystrobin similarly failed.

Comparison 4

As a comparison to Example 4 a sample was prepared which contained oleyl alcohol in water at a lower concentration (10% w/w) than the microencapsulated sample (23% w/w). This sample formed two clear layers. The addition of solvent and a typical emulsifier led to the formation of emulsions that were stable for short time periods however these separated after one hour and they were not found to be stable when incorporated into a commercial suspension concentrate of azoxystrobin. Even an aqueous composition containing only 3% w/w of oleyl alcohol proved similarly unstable.

Attempts to "build-in" the adjuvant at a concentration of 3% w/w to a composition containing 3% w/w fomesafen similarly failed.

The invention claimed is:

1. An aqueous agrochemical concentrate composition comprising (a) a non-encapsulated aqueous solution or dispersion of an agrochemical where the concentration of the agrochemical in the concentrate is from 1 to 500 g/l and (b) a suspension in said aqueous solution or dispersion of a microencapsulated liquid, water-insoluble, bioperformance-enhancing adjuvant for said agrochemical; wherein the adjuvant is a compound of formula (I) or an alkoxylated derivative thereof $$R—X \qquad (I)$$

wherein R is a branched or straight chain alkyl or alkenyl group having from 12 to 20 carbon atoms and X is hydroxy; primary, secondary, tertiary or quaternary amine; amine oxide; phosphonate; phosphate; phosphate ester; thiol; sulphoxide; sulphone; sulphonate; sulphate; a heterocyclic moiety; glucoside; polyglucoside or alkylated glucoside; sarcosinate; betaine; amidoamine; carboxylic acid; amide; ester; ether sulphate; ether amine; ether carboxylate; and ether phosphonate; and the adjuvant has a Hydrophile/Lipophile balance (HLB) of 9 or less.

2. A composition according to claim 1 wherein the group —X is alkoxylated.

3. A composition according to claim 2 wherein the alkoxy group contains from 2 to 4 carbon atoms.

4. A composition according to claim 1 wherein the adjuvant has an average of 1 to 2 ethoxy groups per adjuvant molecule or from 1 to 20 propoxy or butoxy groups per adjuvant molecule.

5. A composition according to claim 1 wherein R is an optionally alkoxylated branched or straight chain alkyl or alkenyl group containing from 16 to 20 carbon atoms.

6. A composition according to claim 5 wherein R is an optionally alkoxylated $C_{18}$ branched chain alkyl or $C_{18}$ alkenyl group.

7. A composition according to claim 6 wherein R is optionally alkoxylated oleyl or isostearyl.

8. A composition according to claim 1 wherein the ratio of the adjuvant to the agrochemical is from 1:50 to 200:1.

9. A composition according to claim 1 wherein the adjuvant is dissolved in a solvent prior to encapsulation.

10. A composition according to claim 1 wherein the adjuvant has the formula (II)

$$R_1—(CO)_m—O—[—R_2O—]_n—R_3 \qquad (II)$$

wherein $R_1$ is a $C_{16}$ to $C_{20}$ straight or branched chain alkyl or alkenyl group, $R_2$ is ethylene or isopropylene, n is from 8 to 30 and m is 0 or 1 and when $R_2$ is ethylene, $R_3$ is a $C_1$ to $C_7$ alkyl group and when $R_2$ is isopropylene, $R_3$ is hydrogen or a $C_1$ to $C_7$ alkyl group.

* * * * *